United States Patent
Nunez et al.

(10) Patent No.: US 10,213,537 B2
(45) Date of Patent: Feb. 26, 2019

(54) VENTRICULAR ASSIST DEVICES AND INTEGRATED SENSORS THEREOF

(71) Applicant: HeartWare, Inc., Miami Lakes, FL (US)

(72) Inventors: Nathalie Jeannette Nunez, Doral, FL (US); Timothy McSweeney, South Miami, FL (US)

(73) Assignee: HeartWare, Inc., Miami Lakes, FL (US)

( * ) Notice: Subject to any disclaimer, the term of this patent is extended or adjusted under 35 U.S.C. 154(b) by 0 days.

(21) Appl. No.: 15/652,793

(22) Filed: Jul. 18, 2017

(65) Prior Publication Data

US 2018/0021497 A1    Jan. 25, 2018

Related U.S. Application Data (60) Provisional application No. 62/363,927, filed on Jul. 19, 2016.

(51) Int. Cl.
*A61M 1/10* (2006.01)
*A61M 1/12* (2006.01)

(52) U.S. Cl.
CPC ............ *A61M 1/122* (2014.02); *A61M 1/101* (2013.01); *A61M 1/1012* (2014.02); *A61M 1/1029* (2014.02); *A61M 1/1086* (2013.01); *A61M 2205/0244* (2013.01); *A61M 2205/3331* (2013.01); *A61M 2205/3334* (2013.01); *A61M 2230/30* (2013.01)

(58) Field of Classification Search
None
See application file for complete search history.

(56) References Cited

U.S. PATENT DOCUMENTS

| 4,690,002 A | 9/1987 | Hubbard et al. |
| 4,989,609 A | 2/1991 | Smith et al. |

(Continued)

FOREIGN PATENT DOCUMENTS

| WO | WO9409835 A1 | 5/1994 |
| WO | WO2016011156 A1 | 1/2016 |

OTHER PUBLICATIONS

International Search Report and Written Opinion dated Sep. 20, 2017, for corresponding PCT/US2017/042576 filed on Jul. 18, 2017, 10 pages.

*Primary Examiner* — Brian T Gedeon
(74) *Attorney, Agent, or Firm* — Christopher & Weisberg, P.A.

(57) ABSTRACT

A ventricular assist device for intraventricular placement inside a heart of a mammalian subject includes a pump including a housing having an inlet end, an inlet at the inlet end, and an outlet. The pump further includes a moveable element disposed in the pump housing for pumping blood from the inlet to the outlet. A base member is included as well as a spacer member connected to the pump housing and the base member. The base member is positioned a distance from the inlet end of the pump housing to define a gap therebetween. One or more sensor elements are mounted to at least one from the group consisting of the base member and the housing, the one or more sensor elements being configured to measure one or more blood parameters prevailing within the gap during operation of the pump.

11 Claims, 6 Drawing Sheets

(56) References Cited

U.S. PATENT DOCUMENTS

| | | |
|---|---|---|
| 6,176,822 B1 | 1/2001 | Nix et al. |
| 6,295,877 B1 | 10/2001 | Aboul-Hosn et al. |
| 6,422,990 B1 | 7/2002 | Prem |
| 6,942,611 B2 | 9/2005 | Siess |
| 6,969,345 B2 | 11/2005 | Jassawalla et al. |
| 7,258,679 B2 | 8/2007 | Moore et al. |
| 7,317,951 B2 | 1/2008 | Schneider et al. |
| 7,520,850 B2 | 4/2009 | Brockway |
| 7,691,046 B2 | 4/2010 | Sullivan |
| 7,976,271 B2 | 7/2011 | LaRose et al. |
| 8,834,344 B2 | 9/2014 | Aboul-Hosn et al. |
| 8,876,685 B2 | 11/2014 | Crosby et al. |
| 9,050,418 B2 | 6/2015 | Schima et al. |
| 9,173,984 B2 | 11/2015 | LaRose et al. |
| 2006/0079786 A1 | 4/2006 | Stofer et al. |
| 2008/0133006 A1* | 6/2008 | Crosby .......... A61M 1/101 623/3.13 |
| 2014/0100414 A1 | 4/2014 | Tamez et al. |
| 2015/0038770 A1* | 2/2015 | Colella .......... A61M 1/122 600/16 |
| 2016/0015878 A1 | 1/2016 | Graham et al. |

\* cited by examiner

VENTRICULAR ASSIST DEVICES AND INTEGRATED SENSORS THEREOF

CROSS-REFERENCE TO RELATED APPLICATION

This application is to and claims priority to U.S. Provisional Patent Application Ser. No. 62/363,927, filed Jul. 19, 2016, entitled VENTRICULAR ASSIST DEVICES AND INTEGRATED SENSORS THEREOF, the entirety of which is incorporated herein by reference.

STATEMENT REGARDING FEDERALLY SPONSORED RESEARCH OR DEVELOPMENT n/a

TECHNICAL FIELD

The present invention relates to blood pumps usable as implantable ventricular assist devices and, more particularly, to improved blood pump designs with one or more integrated sensors.

BACKGROUND

In certain diseased states, the heart lacks sufficient pumping capacity to maintain adequate blood flow to the body's organs and tissues. For example, conditions such as ischemic heart disease and hypertension may leave the heart unable to fill and pump efficiently. This condition, also called congestive heart failure, may lead to serious health complications, including respiratory distress, cardiac asthma, and even death. In fact, congestive heart failure is one of the major causes of death in the Western World.

This inadequacy of the heart can be alleviated by providing a mechanical pump, also referred to as a ventricular assist device ("VAD"), to supplement the pumping action of the heart. VADs may be used to assist the right ventricle, the left ventricle, or both. For example, a VAD may assist the left ventricle by mechanically pumping oxygenated blood from the left ventricle into the aorta.

U.S. Pat. No. 7,976,271 and U.S. Publication No. 2014/0100414 ("the 414 Publication"), the disclosures of which are hereby incorporated by reference herein and copies of which are annexed hereto respectively as exhibits A and B, disclose certain centrifugal blood pumps that can be used as ventricular assist devices. When implanted, these and other implantable pumps, typically have an inlet that communicates with a ventricle of a patient and an outlet that communicates with an aorta via a flexible conduit which is disposed external to the heart. A pumping element typically resides outside of the heart and urges oxygenated blood from the ventricle to the aorta.

U.S. Pat. No. 9,050,418 ("the '418 patent"); U.S. Pat. No. 9,173,984 ("the '984 patent"); U.S. Publication No. 2016/0015878 ("the '878 Publication"), the disclosures of which are hereby incorporated herein by reference and copies of which are annexed hereto as respectively as exhibits C, D and E, disclose certain axial flow blood pumps that can be used as ventricular assist devices. When implanted, these and other implantable pumps, typically have an inlet that communicates with a ventricle of a patient and an outlet that communicates with an aorta via an outflow cannula that extends through the ventricle and into the aorta. A pumping element typically resides within the heart and urges oxygenated blood from the ventricle to the aorta.

When the above-mentioned pumps and other pumps are implanted and in operation, it is desirable to monitor certain parameters to detect abnormal operating conditions and to determine how a pump affects its surrounding environment. For example, flow information can be obtained directly via an ultrasonic flow sensor or indirectly via a pressure sensor. Such information can be used to provide feedback for control of the pump and to detect a blockage or a situation where the pump outpaces a ventricle's blood supply leading to a suction condition. Certain existing VADs are fitted with sensors for detecting some of these parameters. However, despite considerable effort devoted to improvements of such VADs, still further improvement would be desirable.

SUMMARY

In one embodiment of the present invention, a ventricular assist device for intraventricular placement inside a heart of a mammalian subject includes a pump including a housing having an inlet end, an inlet at the inlet end, and an outlet. The pump further includes a moveable element disposed in the pump housing for pumping blood from the inlet to the outlet. A base member is included as well as a spacer member connected to the pump housing and the base member. The base member is positioned a distance from the inlet end of the pump housing to define a gap therebetween. One or more sensor elements are mounted to at least one from the group consisting of the base member and the housing, the one or more sensor elements being configured to measure one or more blood parameters prevailing within the gap during operation of the pump.

In another aspect of this embodiment, the one or more sensor elements include a first sensor element mounted to the pump housing and a second sensor element mounted to the base member.

In another aspect of this embodiment, the first and second sensor elements are ultrasonic transducers.

In another aspect of this embodiment, the pump inlet has a major longitudinal axis, and wherein the ultrasonic transducers are disposed on the base member and pump housing, and during use, ultrasonic waves emitted from the ultrasonic transducers and passing between the ultrasonic transducers cross the major longitudinal axis of the inlet.

In another aspect of this embodiment, the first and second sensor elements include an ultrasonic flow sensor, and wherein the device further includes a third sensor element connected to the base member, the third sensor element being a pressure sensor.

In another aspect of this embodiment, the one or more sensing elements include an ultrasonic transducer mounted on at least one from the group consisting of the pump housing and the base element, the other one from the group consisting of the pump housing and the base element has a reflective surface disposed across the gap from the ultrasonic transducer.

In another aspect of this embodiment, the pump inlet has a major longitudinal axis, the ultrasonic transducer and the reflective surface being disposed on the base member and pump housing, and wherein ultrasonic waves emitted from the ultrasonic transducer and passing from the ultrasonic transducer to the reflective surface and back to the transducer will cross the major longitudinal axis of the inlet.

In another aspect of this embodiment, the one or more sensor elements include a pressure sensor.

In another aspect of this embodiment, the base member has a first end facing toward the pump housing, the base member having a passageway extending within the base member to an opening at the first end of the base member, and wherein the pressure sensor is disposed in the passageway.

In another aspect of this embodiment, the pressure sensor is mounted on a plug and the plug is releasably received in the passageway.

In another embodiment, a ventricular assist device for connection to a heart of a mammalian subject includes a first housing member defining an inlet. A second housing member is coupled to the first housing member and defines an outlet. The first housing member and the second housing member define a flow path extending from the inlet to the outlet. A post extends into the flow path from an inner surface of the second housing thereof and aligned with the inlet. A rotor is sized to be received within the first housing member and the second housing member and defines a bore. The post is received within the bore and the rotor is rotatable about the post to pump blood along the flow path. A sensor is mounted on the post.

In another aspect of this embodiment, the sensor is a pressure sensor.

In another aspect of this embodiment, the post includes a cylindrical portion and a conical portion, and the sensor is mounted on at least one from the group consisting of the cylindrical and conical portions.

In yet another embodiment, a method of assisting the pumping action of a heart of a mammalian subject includes operating a pump of a ventricular assist device to pump blood from a ventricle of a mammalian subject into a gap defined between a pump housing and a base member of the ventricular assist device. A parameter of the blood prevailing in the gap is sensed.

In another aspect of this embodiment, sensing the parameter prevailing in the gap includes sensing the parameter from one or more sensors mounted to at least one from the group consisting of the pump housing and the base member.

In another aspect of this embodiment, the sensor is one from the group consisting of a pressure sensor and an ultrasonic flow sensor.

In another aspect of this embodiment, the parameter is one of from the group consisting of pressure and flow rate.

In another aspect of this embodiment, the method further includes pumping the blood through an outflow cannula in communication with an outlet of the pump housing.

In another aspect of this embodiment, the outflow cannula is configured to at least partially extend through an aortic valve of the mammalian subject and the base member is connected to an apex of the heart.

In another aspect of this embodiment, the base member is connected to the apex of the heart with a sewing ring.

BRIEF DESCRIPTION OF THE DRAWINGS

The features, aspects, and advantages of the present invention will become better understood with regard to the following description, appended paragraphs, and accompanying drawings in which.

DETAILED DESCRIPTION

Figure 1A:
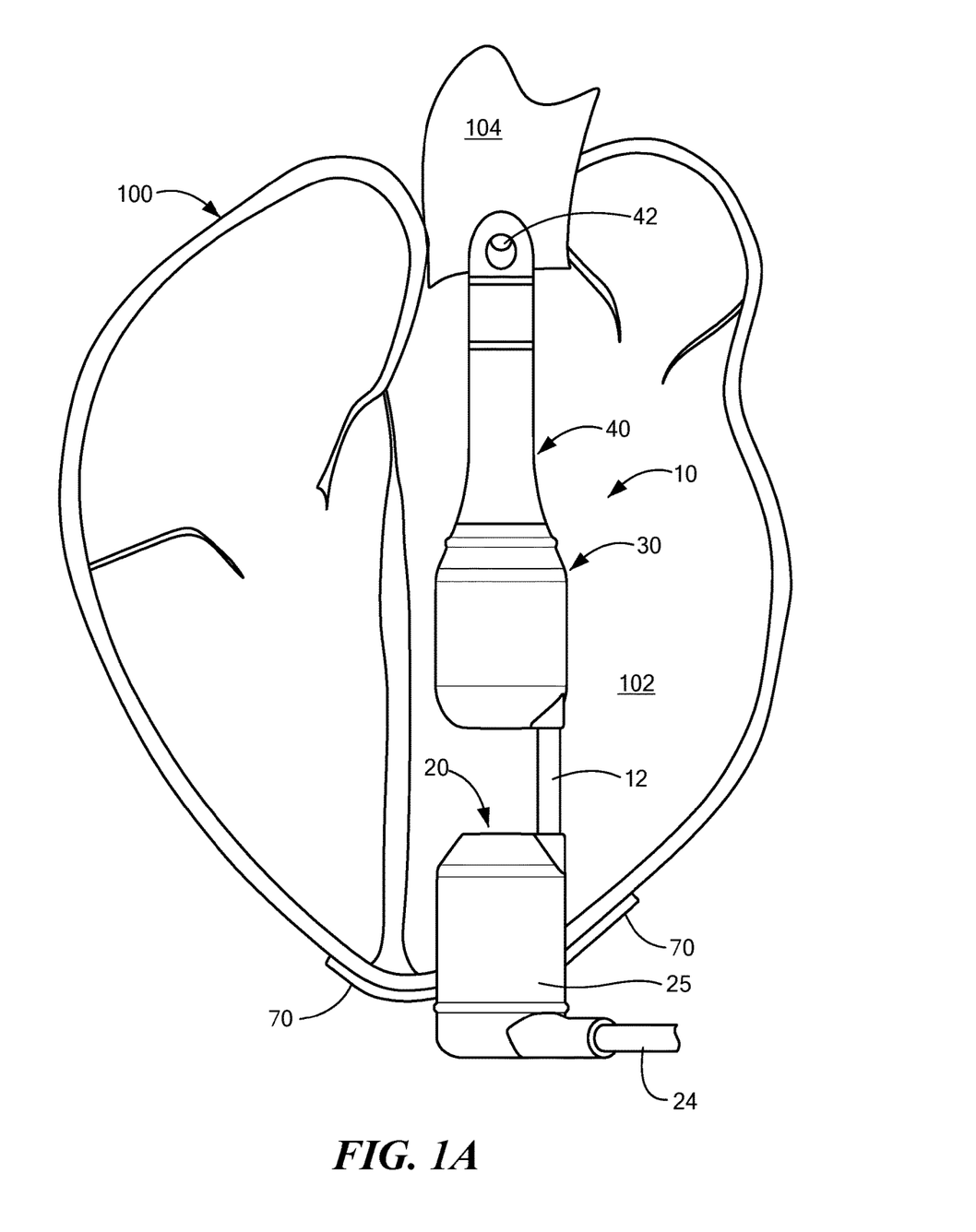
FIG. 1A is an elevational view of a VAD according to one embodiment of the present disclosure as implanted within a heart which is schematically represented.
Figures 1B, 1C:
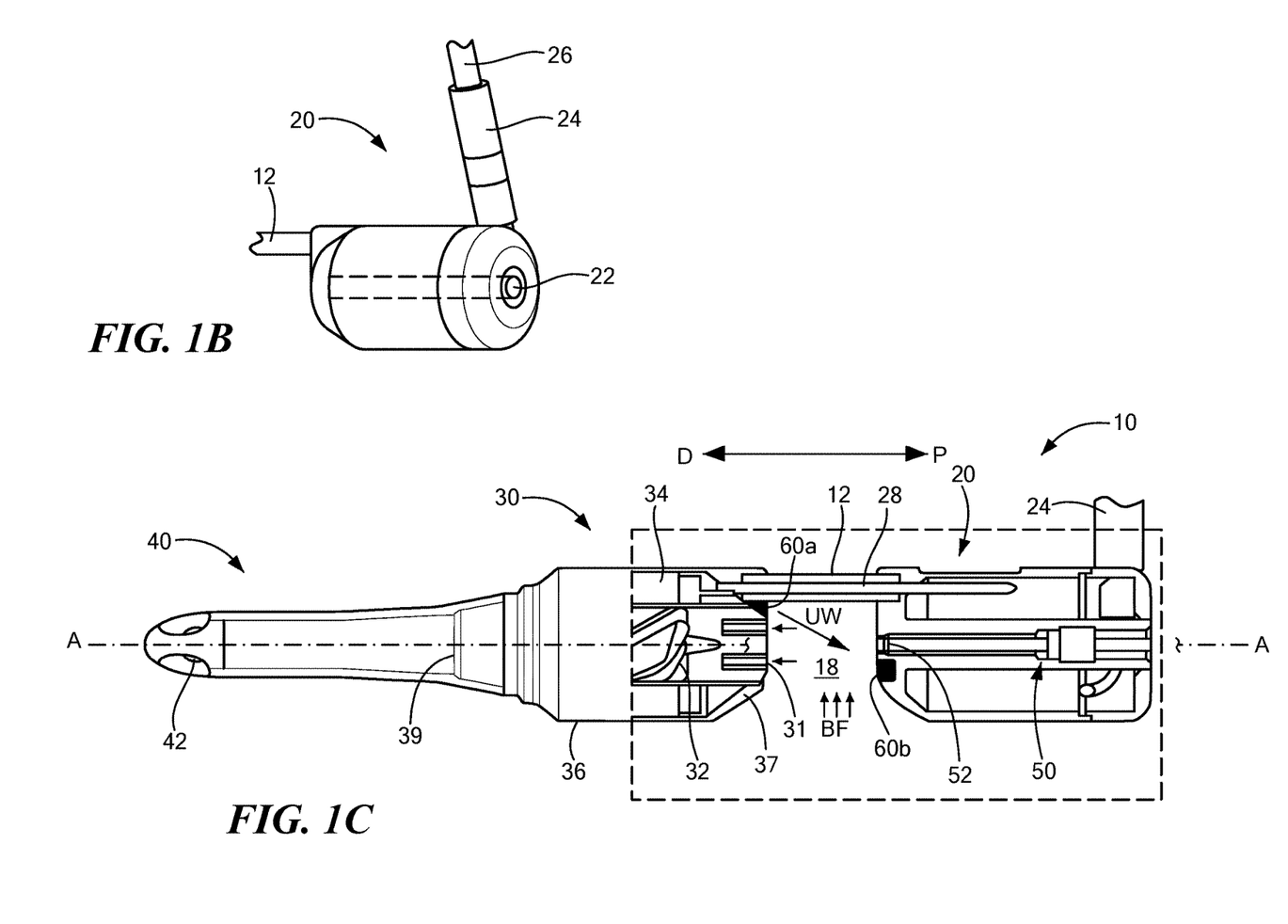
FIG. 1B is an elevational view of a base member of the VAD of FIG. 1A.
FIG. 1C is a partial sectional view of the VAD of FIG. 1A.

Referring now to the drawings in which like reference designators refer to like elements, FIGS. 1A-1C depict an intraventricular, axial flow VAD according to an embodiment of the disclosure and designated generally as "10.". VAD 10 includes a pump 30 comprised of a pump housing 36 and internal components disposed within pump housing 36. Such internal components, as shown in FIG. 1C, include a moveable element or impeller 32 and electrical coils 34 for moving movable element 32 within pump housing 36. Pump housing 36 includes sidewalls 37 that house the internal components and define an inlet 31 at a proximal end thereof and a flow passage extending from an inlet 31 at the proximal end of housing 36 to an outlet 39 at the distal end of housing 36. A hollow outflow cannula 40 communicates with outlet 39 of pump 30 as defined by pump housing 36 and projects distally therefrom. The outflow cannula 40 has outflow apertures The VAD 10 further includes a base member or pedestal 20. Base member 20 is adapted to be engaged by a mounting ring 70 mounted to an outside of a heart 100, as depicted in FIG. 1A. For example, mounting ring 70 may grip an outer surface 25 of base member 20 or by some other engagement means as is known in the art. A projection 24 extends from base member 20 in a direction transverse to an inlet axis A-A of pump 30 and thus transverse to the proximal and distal directions, which are indicated by the arrow D-P in FIG. 1C. An electrical cable 26 is connected to base member 20 by means of projection 24. Electrical cable 26, when implanted, may communicate transcutaneously with an external power source and controller (not shown), such as via a driveline cable or a transcutaneous energy transfer system ("TET"). Alternatively, electrical cable 26, when implanted, may communicate with an internal controller (not shown) also implanted within the patient.

A strut or spacer element 12 mechanically connects base member 20 and pump 30. Such strut 12 is connected to an inlet end or proximal end of pump housing 36 and an inlet facing end or distal end of base member 20. Such connection between strut 12, base member 20 and pump 30 forms a gap 18 between base member 20 and pump 30 through which blood flows prior to entering inlet 31 of pump 30. Electrical conductors 28 from cable 26 extend through base member 20 and through strut 12 to pump 30. The foregoing elements can be generally as disclosed in the '418 patent, the '984 patent, and the '878 Publication.

Base member 20 defines a passageway 22 extending therethrough from its proximal end to its distal end as shown in FIG. 1B. Passageway 22 is closed by a removable closure or plug 50 inserted into the proximal end of base member 20. As shown in FIG. 1C, removable closure 50 can hold a pressure sensor 52 for monitoring pressure and/or determining flow within gap 18. Pressure sensor 52 may be any pressure sensor adapted for use within the body of a mammalian subject. For example, pressure sensor 52 may be any biocompatible microelectromechanical system (MEMS) configured to sense blood pressure in-vivo. When the removable closure 50 is inserted into passageway 22, sensor 52 may be positioned at a terminal end of passageway 22 and near the distal end of base member 20, as best shown in FIG. 1C. Locating sensor 52 at a terminal end of passageway 22 allows sensor 52 to communicate with blood flowing through gap 18 while eliminating the need for blood to travel down passageway 22 to contact sensor 52 which could lead to blood stagnation and clotting therein.

Electrical contacts (not shown) may be exposed within passageway 22 and may be electrically connected to electrical conductors 28 of cable 26 (FIG. 1A) which extend within base member 20. Such electrical contacts can physically interface with electrical contacts on an outer surface of removable closure 50 in order to power the pressure sensor and receive signals therefrom. Alternatively, removable closure 50 may include a passive element (not shown), such as a coil, that may provide wireless energy and signal transfer capabilities to the removable closure.

Additional sensor elements are mounted to VAD 10. These sensor elements include ultrasonic flow transducers 60a and 60b which are mounted to pump housing 36 and base member 20, respectively. Such ultrasonic flow transducers 60a, 60b may be any flow transducer adapted for use within the body of a mammalian subject. For example, the ultrasonic flow transducers 60a and 60b can be conventional piezoelectric elements that are adapted to emit ultrasonic waves upon application of an alternating voltage at ultrasonic frequency, and to provide an alternating electrical potential when ultrasonic vibrations impinge on them As depicted in FIG. 1C, sensor element 60a is mounted at or near inlet 31 of pump housing 36 while sensor element 60b is mounted within base member 20 so that ultrasonic waves UW from either element 60a or 60b are received by the other sensor element. In particular, sensor elements 60a and 60b are disposed at opposite sides of inlet axis A-A which extends proximally from inlet 31 of pump 30 toward base member 20. Ultrasonic waves UW propagated by one of such sensor elements traverse inlet axis A-A and, consequently, pass through blood flowing into inlet 31 of pump 30 during operation before such waves UW are received by the other sensor element. Sensor elements 60a and 60b may be electrically connected to conductors 28 of cable 26 which may extend through pump housing 36 and base member 20, respectively, so as to power elements 60a and 60b and receive signals therefrom.

Thus, as described, VAD 10 includes a pressure sensor and ultrasonic flow sensor. This allows inlet flow and pressure conditions to be measured directly and indirectly. In addition, the pressure sensor may be susceptible to drift. However, the redundancy provided by ultrasonic transducers 60a and 60b allows the pressure sensor to be recalibrated in-vivo based on measurements taken by such transducers. In this regard, transducers 60a-b may provide reference data for calculating drift of sensor 52 since ultrasonic transducers tend to be less susceptible to drift. An internal or external controller in communication with sensor 52 and transducers 60a-b may compare their respective measurements to determine an offset value of sensor 52 in reference to data from transducers 60a-b. For example, flow rate data taken from transducers 60a-b may be converted by the controller to values of pressure for comparison to pressure measurements taken by sensor 52. Alternatively, pressure data taken by sensor 52 may be converted by the controller to flow rate values for comparison to flow rate data taken by transducers 60a-b. Once a threshold level of drift is determined, the controller may adjust the outputs of sensor 52 based on the calculated drift.

In a method of use, VAD 10 may be transapically implanted into a heart 100 as described in the aforementioned '878 Publication. As implanted, outflow apertures 42 of outflow cannula 40 are positioned within an aorta 104. In addition, pump 30 and a portion of base member 20 are disposed within a left ventricle 102 as depicted in FIG. 1A. Base member 20 may be secured to an apex of heart 100 via a mounting ring 70 or some other securement device. Passageway 22, which may have been temporarily occluded by a balloon catheter during implantation, is closed via removable closure 50 which holds sensor 52 by inserting removable closure 50 into passageway 22 from a proximal end thereof. Securement of removable closure 50 may be achieved by corresponding threading within passageway 22 and on an end of removable closure 50. When firmly fixed to base member 20, electrical contacts of base member 20 and removable closure 50 may align and interface to form an electrical connection allowing power to be delivered to sensor 52 and signals to be transmitted therefrom.

When pump 30 is powered on, the pressure sensor 52 and ultrasonic transducers 60a and 60b may also be powered on. As blood flows into inlet 31 of pump housing 36 through gap 18, the pressure of such blood is sensed by sensor 52 which generates a corresponding electric signal indicative of the sensed pressure.

In addition, either transducer 60a or 60b is actuated so that ultrasonic waves (UW) are emitted therefrom. These waves UW travel toward the other transducer and have a component of velocity parallel to the direction of blood flow BF entering into inlet 31 from the subject's ventricle 102 via gap 18. The receiving transducer converts the ultrasonic waves to an electric signal. Because the path from the emitting transducer to the receiving transducer has a component parallel to the direction of blood flow BF, the time of flight of the ultrasonic waves UW is influenced by the velocity of the blood according to the well-known Doppler effect. This causes the phase of the received ultrasonic waves UW to vary with the blood velocity, and thus with the flow rate. Also, because pump housing 36, strut 12, and base member 20 are rigid, the geometry of the system is fixed. As used in this disclosure, the term "rigid" should be understood as meaning that these components do not distort in normal operation of the pump to a degree which would appreciably affect the phase difference between the received and emitted ultrasonic waves. The mathematical relationships used to convert phase difference to flow velocity and to convert flow velocity to flow rate, are well known. The circuits used to measure phase difference are also well known and accordingly are not further described herein.

The electrical signals as generated by sensor 52 and transducers 60a-b may be transmitted to an internal or external controller which may further process the signals and store information derived therefrom for later retrieval or real-time display. Such information may allow a clinician and/or patient to continuously monitor prevailing conditions within gap 18, such as instantaneous intraventricular pressure and pump inlet flow rate and pressure.

Other alternative embodiments of the aforementioned devices are contemplated. For example, one embodiment of VAD 10 may only include one of the pressure sensor and the ultrasonic transducers. In another embodiment of VAD 10, a reflective surface may be provided on pump housing 36 in lieu of transducer 60a or on base member 20 in lieu of transducer 60b. In such embodiment, ultrasonic waves from transducer 60a would reflect off of the reflective surface and be transmitted back to the transducer where the waves would be received.

Figure 2:
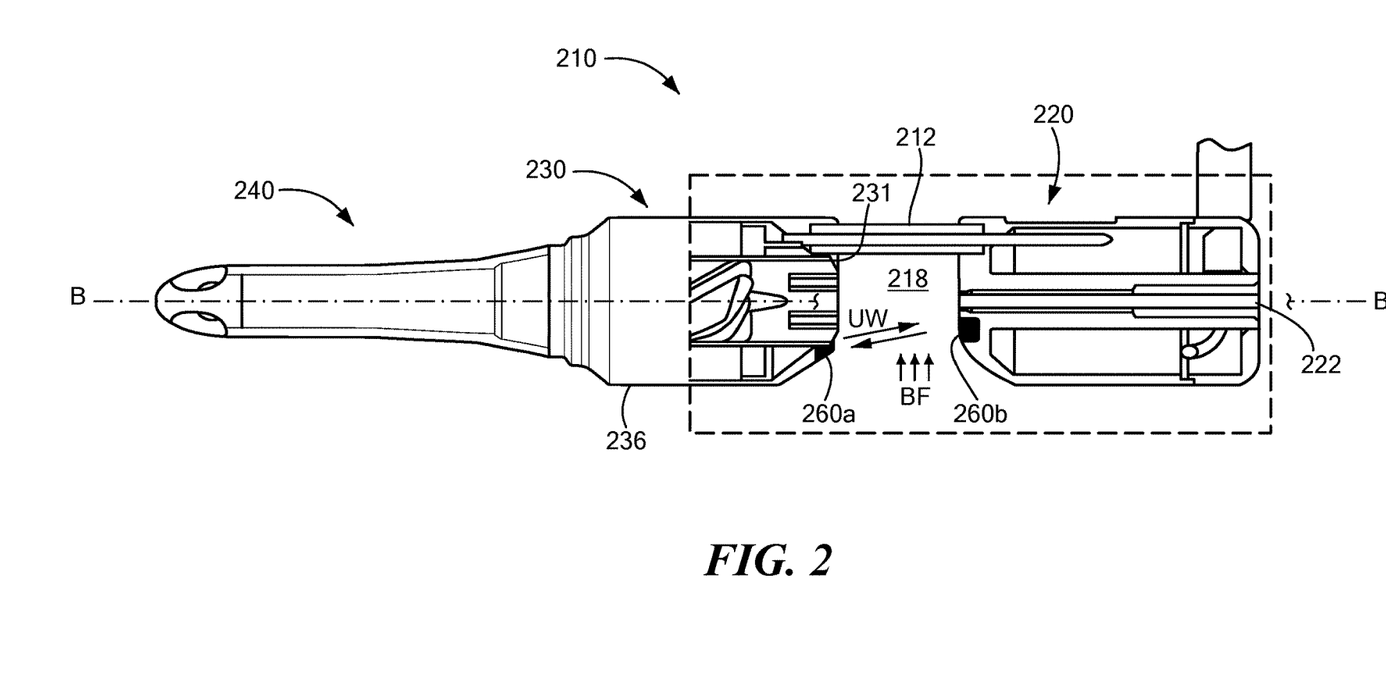
FIG. 2 is a partial sectional view of a VAD according to another embodiment of the present disclosure.

Referring now to FIG. 2, a VAD 200 may similarly include a base member 220, pump 230, outflow cannula 240, and strut 212. Strut 212 connects base member 220 to pump 230 so as to form a gap 218 therebetween. However, unlike VAD 10, VAD 200 includes ultrasonic transducers 260a and 260b mounted to a pump housing 236 and base member 220, respectively, so that transducers 260a-b are disposed on the same side of a pump inlet axis B-B. In this regard, transducer 260b may be positioned closer to the inlet axis B-B so that a component of velocity of an ultrasonic waves UW from either transducer 260a or 260b is transverse to axis B-B and directed either upstream or downstream of blood entering into the gap which itself may have a significant component of velocity transverse to the inlet axis as illustrated by the blood flow arrow BF. The flow of blood passing from the ventricle 102 to inlet 231 of pump 230 will have components of velocity both transverse to the axis B-B and parallel to the axis B-B. Provided that the path of the ultrasound propagating between transducers 260a-b has a component parallel to a component of the flow velocity at some point along the path, the time of flight of the ultrasound waves UW will vary with the flow and a flow measurement can be taken by monitoring the time of flight. The angle between the flow direction and the ultrasound path may vary along the path, and the velocity of the blood typically will vary along the path. However, because the time of flight of the ultrasound waves UW is measured over the path as a whole, the observed time of flight represents an average of these effects, and is well-correlated with the total flow into inlet 231 of pump 230. Further, VAD 200 may or may not include a pressure sensor in base member 220. Also, as mentioned above, a reflective surface can be provided in lieu of one of transducers 260a and 260b.

In an even further embodiment, base member 220 may not include a passageway 222. As such, a pressure sensor, such as sensor 52, or an ultrasonic transducer, such as transducer 260b, may be mounted directly to base member 220 so as to be intersected by axis B-B.

Figure 3:
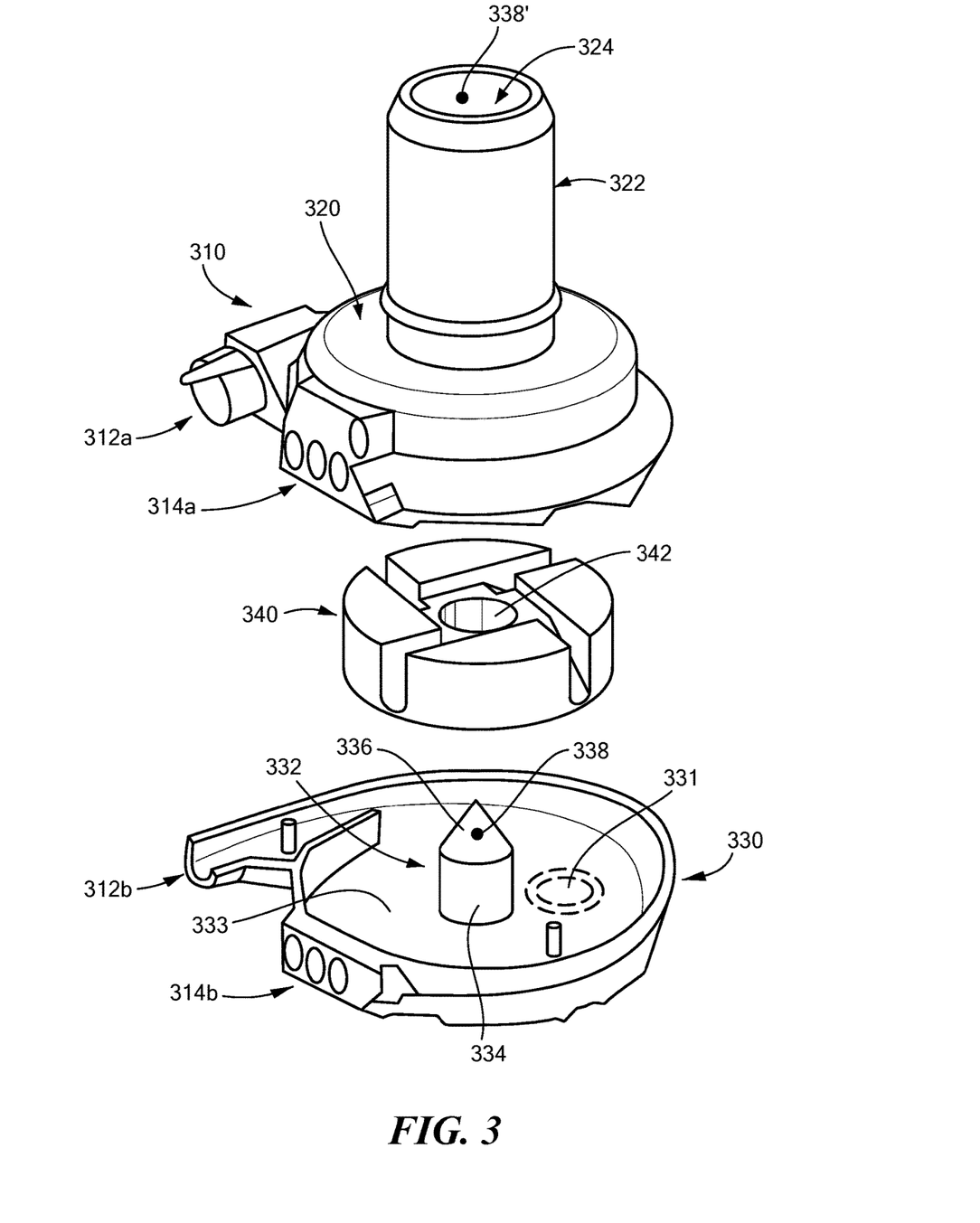
FIG. 3 is an exploded view of a pump used in a VAD in accordance with an embodiment of the present disclosure.

FIG. 3 illustrates a pump 310 of a centrifugal flow VAD according to a further embodiment of the present disclosure. As disclosed in the aforementioned '414 Publication, pump 310 comprises an outer housing that includes a first or upper housing element 320 and a second or lower housing element 330. Housing elements 320 and 330 are formed from biocompatible rigid materials such as titanium, ceramic, or a combination of same.

Upper housing 320 includes an inlet 322 end in the form of a cannula defining an inlet opening 324. Lower housing 330 includes a center-post 332 extending from an internal surface 333 thereof. Center-post 332, as shown, has a cylindrical portion 334 and a conical end portion 336. When upper and lower housings 320, 330 are assembled, center-post 332 extends into inlet opening 324, and a flow path extending from inlet opening 324 to an outflow end 312a-b is cooperatively defined by the housing elements 320, 330. A pressure sensor 338 is disposed within or on a surface of conical portion 336 so that it is exposed to the blood flow path. Pressure sensor 338 may be alternatively located within a surface of cylindrical portion 334. Pressure sensor 338 may be a MEMS as described above or some other conventional pressure sensor for in-vivo blood pressure determination.

A movable element 340, such as the depicted centrifugal-flow impeller, defines an opening 324 which receives center-post 332 so that the moveable element 340 is disposed about center-post 332 between upper and lower housing elements 320 and 330. Moveable element 340 is driven by cooperating permanent magnets in moveable element 340 and a coil set 331 within lower housing 330. When moveable element 340 is disposed about center-post 332, center-post 332 extends from opening 342 of moveable element 340 so that pressure sensor 338 is exposed within cannula 322. This allows blood entering into cannula 322 to flow over pressure sensor 338 before being centrifugally propelled toward outflow end 312a-b by moveable element 340. A permanent magnet may be disposed within center post 332 or elsewhere in the upper or lower housings 320, 330 to prevent contact of center-post 332 and moveable element 340 during operation.

Upper and lower housings 320, 330 may further define a driveline interface 314a-b for connection to an electrical cable which may communicate transcutaneously with an external power source and controller, such as via a driveline cable or a transcutaneous energy transfer system ("TET"). Such interface 314a-b is electrically connected to coil set 331 within housing so that power supplied by the electric cable to coil set 331 generates a magnetic field that cooperates with the permanent magnet in movable element 340, thereby operating moveable element 340. Driveline interface 314a-b may also be electrically connected to pressure sensor 338 on center-post 332 via conductors extending through lower housing 330 and within center post 332. Such conductors may carry power to pressure sensor 338 and carry information signals from pressure sensor 338 to an external controller.

In a method of use, pump 310 is implanted in a mammalian subject such that inlet opening 324 communicates with a ventricle of the subject's heart and so that moveable element 340 is disposed external to the heart. Outflow end 312a-b may communicate with a flexible conduit (not shown) which extends to and communicates with the subject's aorta. When pump 310 is powered on, pressure sensor 338 may also be powered on. As moveable element 340 rotates about center-post 332, blood is drawn from the ventricle into inlet opening 324 and over pressure sensor 338 prior to reaching moveable element 340. The pressure measured by pressure sensor 338 is communicated to an external controller for further processing and storage.

In a further embodiment of pump 310, in addition to pressure sensor 338 being disposed within center-post, an ultrasonic flow sensor may be disposed within the upper and lower housings along the flow path such as the flow sensor described in the aforementioned '414 Publication. Such flow sensor can be used to recalibrate pressure sensor and provide additional flow measurements.

In an even further embodiment of pump 310, a pressure sensor 338' (see FIG. 3) may be disposed within a sidewall of inlet 322 of upper housing 320 in lieu of or in conjunction with sensor 338 being disposed within center-post 332. In this regard, sensor 338' may be exposed to the blood flowing into the inlet cannula 322 and can detect pressure conditions of blood flowing into inlet 322. Conductors (not shown) may be disposed within the sidewall of inlet cannula 322 and may interconnect pressure sensor 338' with a driveline cable connected to driveline interface 314b.

FIGS. 4A-4D depicts a pedestal plug 450 according to a further embodiment of the present disclosure. Pedestal plug 450 is similar to plug 50 in that it is securable to a pedestal of a VAD, such as pedestal 420 shown in FIG. 4D, and is operable to measure blood pressure within a gap between such pedestal 420 and a pump. In this regard, pedestal plug 450 is generally an elongate structure that includes a sensor module 460 at a distal end and a tool engagement portion 452 at a proximal end. Tool engagement portion 452 includes a tool opening 454 that is configured to receive a tool, such as a wrench, driver or the like. Additionally, tool engagement portion 452 may be externally threaded so as to interface with internal threads within pedestal 420 allowing plug 450 to be secured thereto. However, other fixation means known in the art are contemplated.

Sensor module 460 includes a sensor housing 464 that houses various components therein. Such components may include a substrate 465, MEMS pressure die 466, and an ASIC chip 468. As shown in FIG. 4C, die 466 and chip 468 are separately connected to substrate 465. However in some embodiments, die 466 and chip 468 may be provided in an integrated package. A diaphragm 462 covers die 466 and chip 468 at a distal end of housing 464 and acts as a sensing element that interfaces with a patient's blood. Diaphragm 462 communicates with die 466 so that pressure detected by diaphragm 462 is converted to electrical signals which may be communicated to an internal or external controller.

Figure 4A:
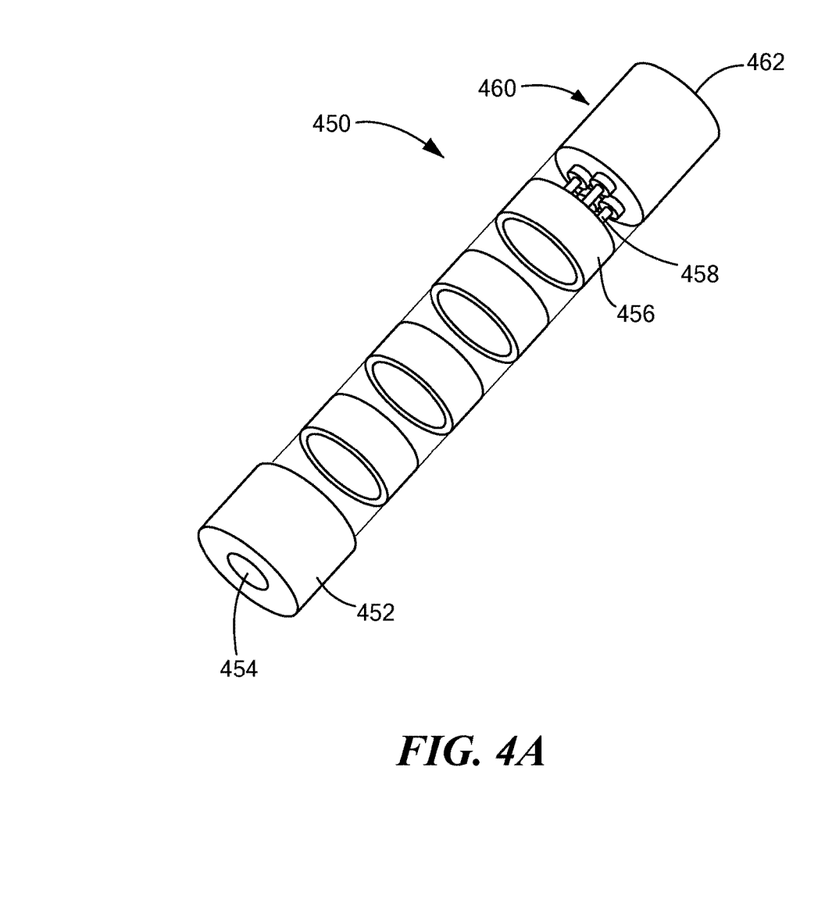
FIG. 4A is perspective partially transparent view of a pedestal plug according to an embodiment of the present disclosure.
Figure 4B:
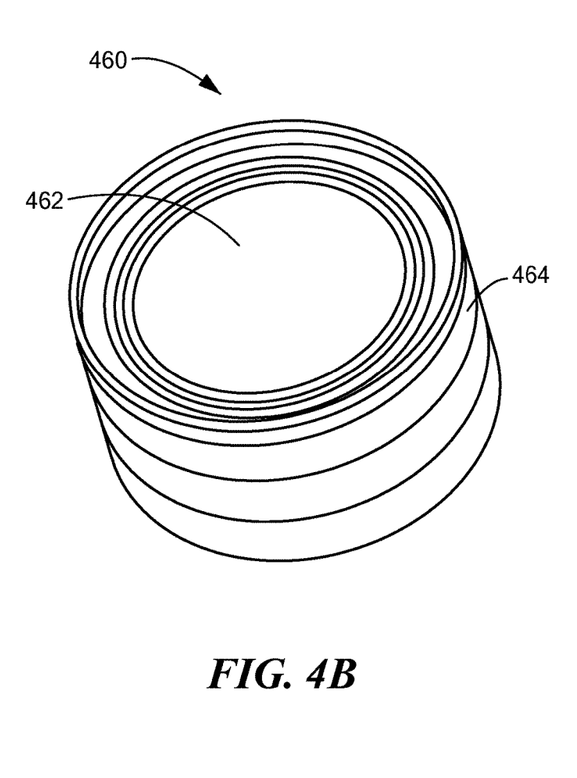
FIG. 4B is a perspective view of a sensor module of the pedestal plug of FIG. 4A.
Figure 4C:
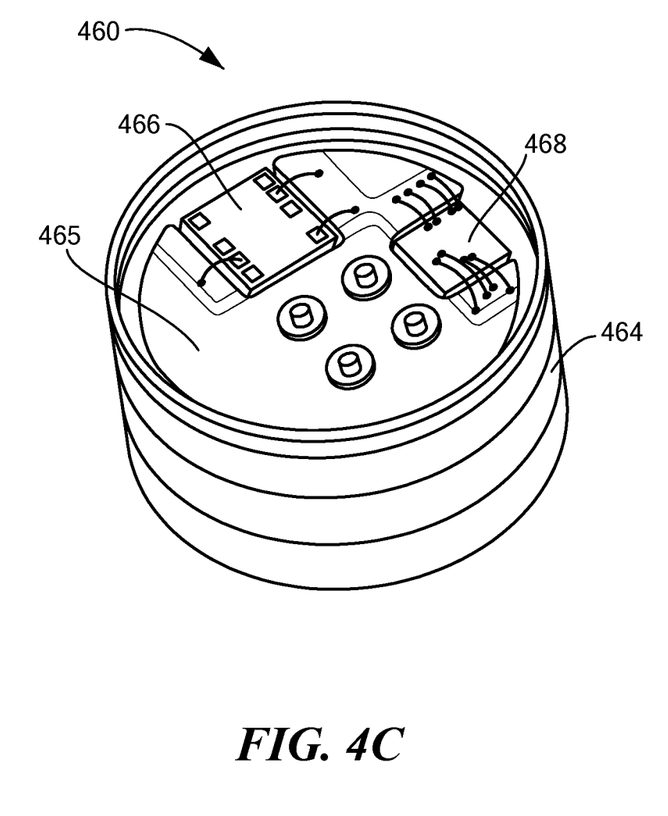
FIG. 4C is a perspective view of the sensor module of FIG. 4B with a diaphragm thereof being removed.

Conductive bands 456 are disposed between sensor module 460 and engagement portion 452, as best shown in FIG. 4A. Such bands 456 are electrically connected to conductors 458 which extend through a proximal end of sensor module housing 464 and are electrically connected to die 466 and chip 468 via substrate 465. Conductive bands 456, tool engagement portion 452, and sensor module 460 may be connected into a single integrated structure by filler material, such as a biocompatible, insulating polymer that joins each of these components together. In this regard, outer surfaces of the conductive bands 456 are preferably exposed.

Figure 4D:
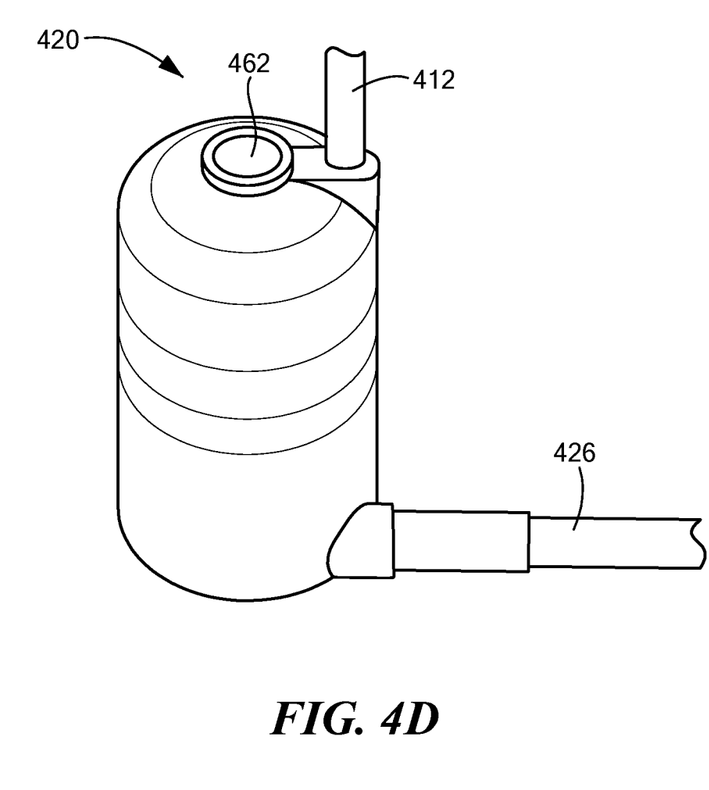
FIG. 4D is perspective view of a pedestal of a VAD according to another embodiment of the present disclosure housing the pedestal plug of FIG. 4A.

FIG. 4D depicts plug 450 secured to a pedestal 420. Pedestal 420 is similar to pedestal 20 in that it is connected to a pump, such as pump 30, via a strut 412. In addition, pedestal 420 is electrically connected to a cable 426 and includes a passageway configured to receive plug 450. The passageway may include electrical contacts (not shown) that interface with the exposed outer surfaces of conductive bands 456 when plug 450 is disposed therein so as to help provide power to plug 450. In this regard, plug 450 may be secured to pedestal 420 by rotating plug 450 with a tool so that threads of plug 450 and pedestal 420 engage. Conductive bands 456, which provide plug with a 360 degree conductive perimeter, helps ensure that plug is electrically connected to pedestal regardless of the angular orientation of plug 450 after being secured to pedestal 420 via threaded engagement. Once plug is secured to pedestal, diaphragm 462 may be positioned at a terminal end of the passageway of pedestal 420 so as to be capable of measuring blood pressure within a gap between pedestal 420 and a blood pump.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. A ventricular assist device for intraventricular placement inside a heart of a mammalian subject comprising:
   a pump including a housing having an inlet end, an inlet at the inlet end, and an outlet, the pump further including a moveable element disposed in the pump housing for pumping blood from the inlet to the outlet;
   a base member;
   a spacer member connected to the pump housing and the base member, the base member being positioned a distance from the inlet end of the pump housing to define a gap therebetween; and
   one or more sensor elements mounted to at least one from the group consisting of the base member and the housing, the one or more sensor elements being configured to measure one or more blood parameters prevailing within the gap during operation of the pump, the one or more sensor elements include an ultrasonic transducer mounted on at least one from the group consisting of the pump housing and the base element, the other one from the group consisting of the pump housing and the base element has a reflective surface disposed across the gap from the ultrasonic transducer.

2. The device of claim 1, wherein the one or more sensor elements include a first sensor element mounted to the pump housing and a second sensor element mounted to the base member.

3. The device of claim 2, wherein the first and second sensor elements are ultrasonic transducers.

4. The device of claim 3, wherein the pump inlet has a major longitudinal axis, and wherein the ultrasonic transducers are disposed on the base member and pump housing, and during use, ultrasonic waves emitted from the ultrasonic transducers and passing between the ultrasonic transducers cross the major longitudinal axis of the inlet.

5. The device of claim 1, wherein the first and second sensor elements include an ultrasonic flow sensor, and wherein the device further includes a third sensor element connected to the base member, the third sensor element being a pressure sensor.

6. The device of claim 1, wherein the pump inlet has a major longitudinal axis, the ultrasonic transducer and the reflective surface being disposed on the base member and pump housing, and wherein ultrasonic waves emitted from the ultrasonic transducer and passing from the ultrasonic transducer to the reflective surface and back to the transducer will cross the major longitudinal axis of the inlet.

7. The device of claim 1, wherein the one or more sensor elements include a pressure sensor.

8. The device of claim 7, wherein the base member has a first end facing toward the pump housing, the base member having a passageway extending within the base member to an opening at the first end of the base member, and wherein the pressure sensor is disposed in the passageway.

9. The device of claim 8, wherein the pressure sensor is mounted on a plug and the plug is releasably received in the passageway.

10. A ventricular assist device for connection to a heart of a mammalian subject, comprising:
    a first housing member defining an inlet
    a second housing member coupled to the first housing member and defining an outlet,
    the first housing member and the second housing member defining a flow path extending from the inlet to the outlet;
    a post extending into the flow path from an inner surface of the second housing thereof and aligned with the inlet;
    a rotor sized to be received within the first housing member and the second housing member and defining a bore, the post being received within the bore, the rotor being rotatable about the post to pump blood along the flow path; and the post includes a cylindrical portion and a conical portion, and the sensor is mounted on at least one from the group consisting of the cylindrical and conical portions.

11. The device of claim 10, wherein the sensor is a pressure sensor.

\* \* \* \* \*